(12) United States Patent
Fung et al.

(10) Patent No.: US 7,998,743 B2
(45) Date of Patent: Aug. 16, 2011

(54) PANEL OF BIOMARKERS FOR PERIPHERAL ARTERIAL DISEASE

(75) Inventors: Eric T. Fung, Los Altos, CA (US); John Cooke, Palo Alto, CA (US); Fujun Zhang, Fremont, CA (US); Andrew Wilson, Glen Iris (AU)

(73) Assignees: Vermillion, Inc., Austin, TX (US); Board of Trustees of the Leland Stanford Junior University, Palo Alto, CA (US)

( * ) Notice: Subject to any disclaimer, the term of this patent is extended or adjusted under 35 U.S.C. 154(b) by 679 days.

(21) Appl. No.: 11/934,008

(22) Filed: Nov. 1, 2007

(65) Prior Publication Data

US 2008/0171396 A1   Jul. 17, 2008

Related U.S. Application Data

(60) Provisional application No. 60/863,951, filed on Nov. 1, 2006.

(51) Int. Cl.
*G01N 33/00* (2006.01)
*G06F 19/00* (2011.01)
(52) U.S. Cl. .................. 436/86; 436/63; 702/19; 702/1
(58) Field of Classification Search .................. 436/63, 436/86; 702/19, 1
See application file for complete search history.

(56) References Cited

U.S. PATENT DOCUMENTS
2004/0121343 A1 * 6/2004 Buechler et al. ................. 435/6

FOREIGN PATENT DOCUMENTS
EP           1 615 036 A1     1/2006

OTHER PUBLICATIONS

O'Hare, A.M., et al.; "Cystatin C and incident peripheral arterial disease events in the elderly," 2005, *Arch. Intern. Med.*, vol. 165, pp. 2666-2670.
Saijo, Y., et al.; "Relationships of $\beta_2$-microglobulin to arterial stiffness in Japanese subjects," 2005, *Hypertens. Res.*, vol. 28, No. 6, pp. 505-511.
Thongboonkerd, V., et al.; "Proteomic analysis reveals alterations in the renal Kallikrein pathway during hypoxia-induced hypertension," 2002, *J. Biol. Chem.*, vol. 277, No. 33, pp. 34708-34716.

(Continued)

*Primary Examiner* — Walter D Griffin
*Assistant Examiner* — Christine T Mui
(74) *Attorney, Agent, or Firm* — Edwards Angell Palmer & Dodge LLP; Peter F. Corless; Melissa Hunter-Ensor, Esq.

(57) ABSTRACT

The invention provides biomarkers including $\beta$-2-microglobulin, Cystatin C, hsCRP and glucose as well as methods for using the biomarkers for diagnosing and/or assessing the risk of peripheral artery disease in a subject. In some embodiments, the subject being tested may be suffering from or at risk of other circulatory diseases, including coronary artery disease. Hemoglobin A1c or other proxies for measuring glucose levels may be substituted for or measured in addition to glucose in the context of the present invention.

11 Claims, 5 Drawing Sheets

OTHER PUBLICATIONS

Nedelkov, Dobrin, et al., "Design and use of multi-affinity surfaces in biomolecular interaction analysis-mass spectrometry (BIA/MS): a step toward the design of SPR/MS arrays," *Journal of Molecular Recognition*, vol. 16, pp. 15-19 (2003).

Schillinger, Martin, et al., "Joint Effects of C-Reactive Protein and Glycated Hemoglobin in Predicting Future Cardiovascular Events of Patients With Advanced Atherosclerosis," *Circulation AHA Journals*, pp. 2323-2328 (Nov. 11, 2003).

Standl, E., et al., "Predictors of 10-year macrovascular and overall mortality in patients with NIDDM: the Munich General Practioner Project," *Diabetologia*, vol. 39, pp. 1540-1545, (1996).

\* cited by examiner

FIGURE 3. Coronary Disease Risk Prediction Score Sheet for Women based on LDL Cholesterol Level Step 1:

| Age | |
|---|---|
| Years | Points |
| 30-34 | -9 |
| 35-39 | -4 |
| 40-44 | 0 |
| 45-49 | 3 |
| 50-54 | 6 |
| 55-59 | 7 |
| 60-64 | 8 |
| 65-69 | 8 |
| 70-74 | 8 |

Step 2:

| LDL-Cholesterol | | |
|---|---|---|
| mg/dL | mm/L | Points |
| <100 | <2.59 | -2 |
| 100-129 | 2.60-3.36 | 0 |
| 130-159 | 3.37-4.14 | 0 |
| 160-189 | 4.15-4.91 | 2 |
| >190 | >4.92 | 2 |

Step 3:

| HDL-Cholesterol | | |
|---|---|---|
| mg/dL | mm/L | Points |
| <35 | <0.90 | 5 |
| 35-44 | 0.91-1.16 | 2 |
| 45-49 | 1.17-1.29 | 1 |
| 50-59 | 1.30-1.55 | 0 |
| >60 | >1.56 | -2 |

FIGURE 3 (cont.)

Step 4:

| Blood Pressure | | | | | |
|---|---|---|---|---|---|
| Systolic | Diastolic (mmHg) | | | | |
| (mm Hg) | <80 | 80-84 | 85-89 | 90-99 | >=100 |
| <120 | -3 pts | | | | |
| 120-129 | | 0 pts | | | |
| 130-139 | | | 0 pts | | |
| 140-159 | | | | 2 pts | |
| >=160 | | | | | 3 pts |

Step 5:

| Diabetes | |
|---|---|
| | Points |
| No | 0 |
| Yes | 4 |

Step 6:

| Smoker | |
|---|---|
| | Points |
| No | 0 |
| Yes | 2 |

Step 7 (sum from steps 1-6)   Point Total: _____

FIGURE 3 (cont.)

Step 8 (Determine CHD risk from point total)

| Point Total | 10 Yr CHD risk (%) |
|---|---|
| <= -2 | 1 |
| -1 | 2 |
| 0 | 2 |
| 1 | 2 |
| 2 | 3 |
| 3 | 3 |
| 4 | 4 |
| 5 | 5 |
| 6 | 6 |
| 7 | 7 |
| 8 | 8 |
| 9 | 9 |
| 10 | 11 |
| 11 | 13 |
| 12 | 15 |
| 13 | 17 |
| 14 | 20 |
| 15 | 24 |
| 16 | 27 |
| >=17 | >=32% |

Step 9 (Compare to women of the same age)

| Age | Avg 10 yr CHD risk (%) | Low* 10 yr CHD risk (%)* |
|---|---|---|
| 30-34 | <1 | <1 |
| 35-39 | 1 | <1 |
| 40-44 | 2 | 2 |
| 45-49 | 5 | 3 |
| 50-54 | 8 | 5 |
| 55-59 | 12 | 7 |
| 60-64 | 12 | 8 |
| 65-69 | 13 | 8 |
| 70-74 | 14 | 8 |

\*    Low risk was calculated for a woman in the same age, normal blood pressure, LDL cholesterol, 100-129 mg/dL, HDL cholesterol 55 mg/dL, non smoker, no diabetes.

PANEL OF BIOMARKERS FOR PERIPHERAL ARTERIAL DISEASE

CROSS-REFERENCES TO RELATED APPLICATIONS

This application claims priority to U.S. Provisional Patent Application Ser. No. 60/863,951, filed Nov. 1, 2006, the disclosure of which is incorporated herein by reference in its entirety.

FEDERALLY-SPONSORED RESEARCH OR DEVELOPMENT

This invention was made with Government support under contracts HL075774 and HL063685 awarded by the National Institutes of Health. The Government has certain rights in this invention.

BACKGROUND OF THE INVENTION

Peripheral arterial disease (PAD) affects 8 to 12 million individuals in the United States and is also prevalent in Europe and Asia (Allison et al., *Am J Prev Med* 2007; 32:328-33; Hasimu et al., *Hypertens Res* 2006; 29:23-8; Brevetti et al., *J Cardiovasc Med* (Hagerstown) 2006; 7:608-13; Hayoz et al., *J Intern Med* 2005; 258:238-43; Criqui et al., *Circulation* 2005; 112:2703-7). Classically, PAD causes limb fatigue or pain brought on by exertion and relieved by rest, i.e. intermittent claudication, and reduces functional capacity and quality of life (McDermott et al., *Jama* 2004; 292:453-61). It is frequently associated with coronary artery disease (CAD) and cerebral disease (McDermott et al., *Jama* 2004; 292:453-61; Steg et al., *Jama* 2007; 297:1197-206). Patients with PAD are at increased risk from myocardial infarction, stroke, aortic aneurysm, and vascular death, as well as ischemic ulceration and amputation (Steg et al., *Jama* 2007; 297:1197-206; Newman et al., *Arterioscler Thromb Vasc Biol* 1999; 19:538-45).

The high risk of vascular events in PAD is reduced by aggressive risk factor modification. In these individuals, the use of statins, angiotensin converting enzyme inhibitors, and antiplatelet therapy reduces morbidity and mortality (Hankey et al., *Jama* 2006; 295:547-53). Unfortunately, PAD is underdiagnosed and undertreated. In fact, many of those affected do not manifest the classic symptomatology. Classic claudication is only noted by 10-30% of patients (McDermott et al., *Jama* 2004; 292:453-61; Hirsch et al., *Jama* 2001; 286:1317-24) and atypical leg discomfort occurs in 20-40% (McDermott et al., *Jama* 2001; 286:1599-606). Up to 50% of patients do not complain of leg symptoms. However, even these individuals have a reduced lifespan without aggressive treatment (McDermott et al., *Jama* 2004; 292:453-61; Criqui et al., *N Engl J Med* 1992; 326:381-6; Vogt et al., *Jama* 1993; 270:465-9; Newman et al., *J Am Geriatr Soc* 1997; 45:1472-8). In other situations, individuals may be suffering from other circulatory maladies (e.g., coronary artery disease) whose symptoms may obscure a diagnosis of PAD.

BRIEF SUMMARY OF THE INVENTION

In one embodiment, the invention provides a blood test that increases the clinical index of suspicion and allows practitioners to identify patients that merit greater scrutiny for PAD, even where those practitioners lack immediate access to the specialized equipment and trained personnel to perform measurements of limb blood flow and pressure (e.g., the ankle-brachial index or ABI). Patients with elevated scores can be referred to vascular specialists who could provide further evaluation and appropriate management. Intensive risk factor modification confers longevity in these patients and extends freedom from major adverse cardiovascular events (Beckman et al., *Circulation* 2006; 114:861-6). In particular, the blood tests of the invention can distinguish those at greater risk of having PAD and allow for those individually to be selectively triaged for vascular testing (rather than sending all patients for expensive vascular testing).

In another embodiment, the invention provides a method for diagnosing peripheral artery disease in a subject, comprising obtaining measurements of the levels of beta-2-microglobulin (also referred to as "B2M," herein), cystatin C, hsCRP, and at least one biomarker selected from the group consisting of glucose, hemoglobin A1c and glycated hemoglobin; comparing said measurements to a standard, wherein increases in said levels of beta-2-microglobulin, cystatin C, hsCRP, and glucose and/or hemoglobin A1c and/or glycated hemoglobin relative to said standard is associated with an increased risk of peripheral artery disease in a subject; and reporting or recording the results of said comparison. In a related embodiment, the method further comprises determining the risk of coronary artery disease ("CAD") in said subject using, e.g., a score sheet. In one embodiment, the score sheet could be that recommended by the American Heart Association for determining the risk of CAD. In a related embodiment, the risk of CAD in the subject of interest is determined to be low, medium or high. In yet another related embodiment, the subject is affirmatively diagnosed with coronary artery disease. In yet another related embodiment, the subject is being treated for PAD and the method is used to monitor the course of treatment.

In another embodiment, the invention provides a method for diagnosing peripheral artery disease in a subject, comprising obtaining measurements of the levels of beta-2-microglobulin, cystatin C, hsCRP, and at least one biomarker selected from the group consisting of glucose, hemoglobin A1c and glycated hemoglobin; combining the measured levels to derive an index score; comparing said index score with a standard, wherein said comparison identifies a risk of peripheral artery disease in a subject; and reporting or recording the results of said comparison. In a related embodiment, the method further comprises determining the risk of coronary artery disease in said subject. In a related embodiment, the method further comprises determining the risk of coronary artery disease ("CAD") in said subject using, e.g., a score sheet. In one embodiment, the score sheet could be that recommended by the American Heart Association for determining the risk of CAD. In related embodiments, the risk of CAD in the subject of interest is determined to be low, medium or high. In yet another related embodiment, the subject is affirmatively diagnosed with coronary artery disease. In yet another related embodiment, the risk of CAD in the subject is determined to be high. In yet another related embodiment, the subject is being treated for PAD and the method is used to monitor the course of treatment.

In another embodiment, the invention provides a method for diagnosing peripheral artery disease in a patient previously diagnosed with coronary artery disease or a risk thereof, comprising obtaining measurements of the levels of at least one biomarker selected from the group consisting of glucose, hemoglobin A1c and glycated hemoglobin, and at least one additional biomarker selected from the group consisting of β-2-microglobulin, cystatin C, and hsCRP; comparing said measurements to a standard, wherein an increase in said levels of glucose and said at least one additional biomarker relative to said standard is associated with an increased risk of peripheral artery disease in a subject; and reporting or recording the results of said comparison. In a related embodiment, the additional biomarkers are β-2-microglobulin and cystatin C. In another related embodiment, the additional biomarkers are cystatin C and hsCRP. In still another related embodiment, the additional biomarkers are β-2-microglobulin and hsCRP. In yet another related embodiment, only one additional biomarker is selected from the group consisting of β-2-microglobulin, cystatin C, and hsCRP. In still other related embodiments, other suitable biomarkers (e.g., lysozyme) are utilized in addition to the above-mentioned combinations of biomarkers.

In another related embodiment, a computer algorithm is utilized to calculate the index score for assessing risk of peripheral artery disease. In yet another related embodiment, the index score is identified as falling into one of at least three categories of increasing risk. In yet another related embodiment, the index score is categorized as falling into a tertile corresponding to low, medium or high risk of PAD.

In various embodiments, the levels of beta-2-microglobulin, cystatin C, hsCRP, hemoglobin A1c and/or glycated hemoglobin are measured by antibody, activity assays, mass spectrometry, and/or other methods known to those skilled in the art for measuring proteins found in human blood or serum.

In another embodiment, the invention provides a kit useful for determining the risk of PAD in a subject, wherein the kit comprises a solid support comprising a capture reagent that binds beta-2-microglobulin; a solid support comprising a capture reagent that binds C reactive protein (CRP); a solid support comprising a capture reagent that binds Cystatin C; and instructions for using the solid support to detect beta-2-microglobulin, Cystatin C and CRP. In a related embodiment, the the kit comprises a capture reagent that binds beta 2-microglobulin, CRP and Cystatin C. In yet another related embodiment, the kit further comprises reagents for measuring glucose levels, hemoglobin A1c levels and/or glycated hemoglobin levels in a serum sample. In yet another related embodiment, the kit comprises reference standards for beta 2-microglobulin, CRP, and Cystatin C. In yet another related embodiment, the kit comprises reference standards for hemoglobin A1c or glycated hemoglobin.

In another embodiment, the invention provides a software product comprising code that accesses data attributed to a sample, the data comprising levels of at least four biomarkers in the sample, wherein the at least four biomarkers include beta 2-microglobulin, CRP, Cystatin C, and at least one biomarker selected from the group consisting glucose, hemoglobin A1c or glycated hemoglobin; and code that executes a classification algorithm that classifies the peripheral artery disease status of the sample as a function of said levels.

In yet another embodiment, the invention provides the methods, kits and software products provided above, further incorporating materials and methods for the detection of levels of lysozyme C in a subject and correlating those measurements with PAD status.

BRIEF DESCRIPTION OF THE DRAWINGS

FIG. 3 shows an exemplary "score sheet" for determining the risk of coronary artery disease (CAD) in a subject. In this case, the subject is a female and LDL cholesterol levels are measured. American Heart Association score sheets for determining the risk of CAD are well-known in the art.

DETAILED DESCRIPTION OF THE INVENTION

Figure 1:
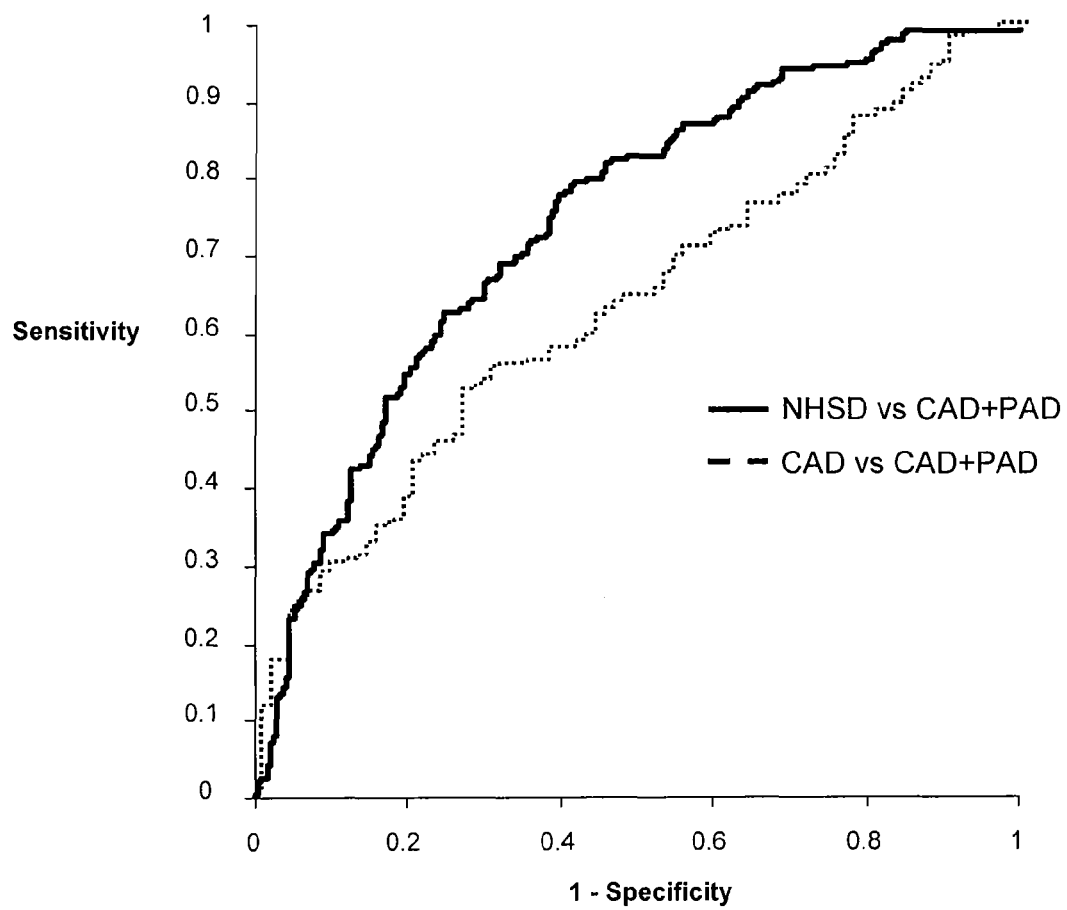
FIG. 1 shows a receiver operated curve (ROC) analysis of a four marker index comparing NHSD (no hemodynamically significant disease, e.g., atherosclerosis) vs CAD+PAD and CAD vs CAD+PAD subjects.

This invention provides panels of multiple biomarkers that are useful for diagnosing peripheral arterial disease. For example, in one embodiment, a four biomarker panel comprising β2M, cystatin C, hsCRP, and glucose is presented that allows clinicians to evaluate the relative risk of PAD even in the background of traditional risk factors (e.g., diabetes). Individuals in the top quartile of the four biomarker panel score had a 7-fold greater risk of PAD. Such a biomarker panel can be used to alert a clinician to the possibility of PAD in patients who might otherwise go undiagnosed.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

The biomarker of this invention were discovered, in part, using SELDI (Surface-enhanced laser desorption ionization). Accordingly, they can be characterized, in part, by their mass-to-charge ratio, the shape of the peak in a mass spectrum and their binding characteristics. These characteristics represent inherent characteristics of the biomolecule and not process limitations in the manner in which the biomolecule is discriminated.

The mass-to-charge ratio of some of the protein biomarkers are provided herein. A particular molecular marker designated, for example, as "M11.7K" has a measured mass-to-charge ratio of 11.7 kD. The mass-to-charge ratios were determined from mass spectra generated on a Ciphergen Biosystems, Inc. PBS II mass spectrometer or a Ciphergen PCS 4000 mass spectrometer. The PBS II is instrument has a mass accuracy of about +/−0.15 percent. Additionally, the instrument has a mass resolution of about 400 to 1000 m/dm, where m is mass and dm is the mass spectral peak width at 0.5 peak height. The PCS4000 instrument has a mass accuracy of about +/−0.12% raw data with an expected externally calibrated mass accuracy of 0.1% and internally calibrated mass accuracy of 0.01%. Additionally, the instrument has a mass resolution of about 1000 to 2000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII or PCS4000, taking the maximum and minimum mass-to-charge-ratio in the cluster, and dividing by two. Accordingly, the masses provided reflect these specifications.

The biomarkers of this invention may be further characterized by the shape of their spectral peak in time-of-flight mass spectrometry.

The biomarkers of this invention are also characterized by their binding characteristics to adsorbent surfaces. The binding characteristics of the biomarkers are also described herein.

Biomarkers for Peripheral Artery Disease

Useful protein biomarkers for peripheral artery disease include β2-microglobulin, Cystatin C, hsCRP and lysozyme C. β2-microglobulin is a 99 amino acid protein derived from a 119 amino acid precursor (GI:179318; SwissProt Accession No. P61769) and is recognized by antibodies available from, e.g., Abcam (catalog AB759) (www.abcam.com, Cambridge, Mass.). Levels of β2-microglobulin less than 1.85 mg/ml are considered within normal limits. Various other features of the biomarkers are described in the Tables presented herein.

TABLE 1

| Marker | P-Value | Up or down regulated in peripheral artery disease | ProteinChip ® assay |
|---|---|---|---|
| β2-microglobulin (M11.7K) (predicted mass: 11,729.17 D) | <0.05 | Up | IMAC-Cu$^{++}$ (fractions 1-3) |
|  | <0.05 | Up | CM10 (fraction 2) |
| Cystatin C (predicted mass: 13,343 D) | <0.05 | Up | CM10 (fraction 1) |
| Lysozyme (i.e., lysozyme C) (predicted mass: 14,692 D) | <0.05 | Up | CM10 (fraction 1) |

The fractions referred to in the last column of Table 1, above, are the fractions in which the biomarkers elute from a QHyper DF column (BioSepra, Cergy, France). The QHyperDF column can be used to purify the biomarkers from plasma, as described in, e.g., U.S. patent application Ser. No. 11/685,146. IMAC-Cu$^{++}$ and CM10 refer to commercially available Proteinchips comprising metal chelating and cation exchange adsorbents, respectively.

In the context of a biomarker panel useful for diagnosing and/or assessing risk of PAD, other metabolites (e.g., glucose) may be measured, as well as other protein biomarkers in addition to (or in lieu of) B2M. For example, C-reactive protein ("CRP," or "hsCRP" for "high sensitivity CRP") is a homopentameric oligoprotein composed of monomeric subunits that are each about 21 kD. The human CRP molecule has a relative molecular weight of about 115 kDa (115,135 Da), and is composed of five identical non-glycosylated polypeptide subunits, each having a relative molecular weight of about 23 kDa (23,027 Da), and each containing 206 amino acid residues (Hirschfield and Pepys *Q J Med* 2003; 96: 793-807). Serum levels of hsCRP are elevated in individuals at risk for peripheral artery disease. Based upon the published literature, the American Heart Association recommends that hsCRP be used to "detect enhanced absolute risk in persons in whom multiple risk factor scoring (based on the Framingham Heart Study global risk scoring system) projects a 10-year CHD risk in the range of 10% to 20%." In this population, hsCRP can be used to determine those at lower or greater risk. Risk would be relatively "low" with hsCRP levels of less than 1 mg/L; "average" at 1-3 mg/L; and "high" at levels greater than 3 mg/L. In addition, one skilled in the art would know how to generate or obtain antibodies for the purpose of measuring CRP in human serum.

Cystatin C (sometimes referred to as cystatin 3) is a cysteine protease inhibitor found in serum that is sometimes used as a biomarker for kidney function. Antibodies useful for detecting cystatin C are readily available. The range of Cystatin C in human serum is between 0.5 and 0.99 mg/dl (see, e.g., Uhlmann E J et al., *Clin Chem.* 2001;47(11):2031-2033).

In one embodiment of a biomarker panel for diagnosing PAD, the protein biomarkers cystatin C, hsCRP and/or beta 2-microglobulin levels in serum are measured in addition to glucose levels. Methods for measuring glucose levels in humans are well-known in the art. Blood glucose is typically measured after fasting (e.g., collected after an 8 to 10 hour fast), and/or as part of an oral glucose tolerance test (OGTT/GTT). Normal fasting levels of glucose are below 100 mg/dl.

Other protein biomarkers such as hemoglobin A1c and/or glycated hemoglobin whose levels may be correlated with glucose levels can also be measured and used in the context of the biomarker panel for PAD described herein. Healthy persons typically have levels of hemoglobin A1c from 4-5.9%. Because higher levels of hemoglobin A1c are associated with higher levels of blood glucose (see, e.g., Koenig R J et al. (1976) *N. Engl. J. Med.* 295 (8):417-20; Larsen et al. (1990). *N. Engl. J. Med.* 323 (15):1021-5), the detection of higher levels of hemoglobin A1c is a useful indicator of increased risk of PAD in a subject according to the diagnostic methods described herein. A variety of kits and methods for the detection of A1c are available and well-known to those of ordinary skill in the art.

Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody (e.g., a monoclonal antibody which binds to an epitope of beta 2-microglobulin) will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where a traditional immunoassay fails to distinguish the forms and fails to specifically detect the useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or a chip. After unbound materials are washed away, the captured analytes are detected and/or measured by mass spectrometry. This method also will also result in the capture of protein interactors that are bound to the proteins or that are otherwise recognized by antibodies and that, themselves, can be biomarkers. Various forms of mass spectrometry are useful for dectecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring beta-2-microglobulin" includes measuring beta-2-microglobulin by means that do not differentiate between various forms of the protein (e.g., certain immunoassays) as well as by means that differentiate some forms from other forms or that measure a specific form of the protein. In contrast, when it is desired to measure a particular form or forms of a protein, e.g., a particular form of beta-2-microglobulin, the particular form (or forms) is specified. For example, "measuring beta-2-microglobulin (M11.7K)" means measuring beta-2-microglobulin M11.7K in a way that distinguishes it from other forms of beta-2-microglobulin.

Detection and Measurement of Biomarkers

The β2-microglobulin, cystatin C, hsCRP and glucose (or hemoglobin A1c) biomarkers of the present invention can be detected by any suitable method. Detection paradigms include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. A biochip generally comprises a solid substrate having a substantially planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. A laser desorption mass spectrometer can be used which employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI, described, for example, in U.S. Pat. Nos. 5,719,060 and 6,225,047, both to Hutchens and Yip. In a related method, one can capture the biomarkers with a solid-phase bound immuno-adsorbent that has antibodies that bind the biomarkers. After washing the adsorbent to remove unbound material, the biomarkers are eluted from the solid phase and detected by applying to a chip (e.g., a SELDI chip) that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Other forms of laser desorption mass spectrometry that can be used to detect the biomarkers of the present invention include Surface-Enhanced Neat Desorption ("SEND") and Surface-Enhanced Photolabile Attachment and Release ("SEPAR"; see, e.g., U.S. Pat. No. 5,719,060).

In another embodiment of the invention, the biomarkers of the invention are measured by a method other than mass spectrometry, or any other method that requires determining the mass of the biomarker. In one such embodiment that does not rely on mass, the biomarkers are measured by immunoassay. Immunoassay requires biospecific capture reagents, such as antibodies, to bind or capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art. Antibodies and methods for detecting beta 2-microglobulin using standard assays are described in the art, e.g., Hilgert et al. (*Folia Biol (Praha)* (1984) 30:369-76). Examples of the use of these antibodies to detect increased levels of beta 2-microglobulin in PAD patients relative to normal patients are provided herein. Similar methods for the immunoassay detection of cystatin C, hsCRP, and other protein biomarkers are also known in the art. Enzyme-linked immunoabsorbent assays (ELISA's) directed at these biomarkers are commercially available from a wide variety of sources, including Dade-Behring and BioCheck.

This invention contemplates traditional immunoassays including, for example, sandwich immunoassays including ELISA or fluorescence-based immunoassays, other enzyme immunoassays and western blot. Nephelometry is an assay done in liquid phase, in which antibodies are in solution.

Binding of the antigen to the antibody results in changes in absorbance, which is measured. In the SELDI-based immunoassay, a biospecific capture reagent for the biomarker is attached to the surface of an MS probe, such as a pre-activated Proteinchip array. The biomarker is then specifically captured on the biochip through this reagent, and the captured biomarker is detected by mass spectrometry.

Measurements of levels of glucose or hemoglobin A1c/glycated hemoglobin in human serum or plasma can be achieved using any of a variety of well-known assays, including commercial kits. For example, glucose test kits are available from a wide variety of vendors, including Abbott and Olympus.

Determination of Subject Peripheral Artery Disease Status

The biomarkers of the invention can be used in diagnostic tests to assess peripheral artery disease status in a subject, e.g., to assess the risk of a patient having peripheral artery disease. The phrase "peripheral artery disease status" includes any distinguishable manifestation of the disease, including non-disease. For example, peripheral artery disease status includes, without limitation, the presence or absence of disease (e.g., peripheral artery disease v. non-peripheral artery disease), the risk of developing disease, the stage of the disease, the progression of disease (e.g., progress of disease or remission of disease over time), the severity of the disease, and the effectiveness or response to treatment of disease.

The correlation of test results with peripheral artery disease status involves applying a classification algorithm of some kind to the results to generate the status. The classification algorithm may be as simple as determining whether or not the amount of beta-2-microglobulin measured is above or below a particular cut-off number. When multiple biomarkers or cardiovascular risk factors (e.g., the age, gender, blood pressure, blood sugar, and blood cholesterol) are used, the classification algorithm may be a linear regression formula. Alternatively, the classification algorithm may be the product of a learning algorithm.

One way to translate biomarker measurements into an assessment of disease risk is to devise a scoring sheet, such as that shown in FIG. 3 (showing how LDL cholesterol levels may be used to determine the likelihood of coronary artery disease). This type of scoring sheet provides cut-off values against which measurements are compared in order to determine how many "points" are assigned to the measurement. For example, a measurement of 170 mg/dL LDL-cholesterol merits 2 points in the scoring sheet (see FIG. 3, Step 2).

The correlation of the results of tests using, e.g., a combined beta 2-microglobulin, CRP, cystatin C and glucose (or hemoglobin A1c) biomarker panel with PAD status generally involves applying a classification algorithm. As discussed above, such an algorithm may be as simple as determining whether the levels of a particular biomarker are above or below a "cut-off" or "threshold" or value. Levels above threshold are considered "high" and may be assigned a higher score value in the context of the algorithm. Levels below the threshold may be considered "low" and may be assigned a lower score value.

In general, the "threshold" value for a biomarker in the context of the present method for assessing PAD status refers to a median value of a range of biomarker levels (e.g., amounts) for a selected subject population. Use of a median value for a selected subject population as a threshold value is suitable for evaluating high and low levels of each of the biomarkers in a panel (e.g., CRP/B2M/CystatinC/glucose) in view of the left skewed distributions of those biomarkers across a population. Thus a "high" biomarker level is a level of biomarker that is greater than this threshold value; a "low" biomarker level is lower than this threshold value. Stated differently, a threshold value is a median value such that a test value above, usually significantly above, the median value is classified as "high" and a test value below, usually significantly below, the median value is classified as "low".

It may also be suitable to divide values of biomarker levels of a subject population into more finely divided groups, e.g., into tertiles, quartiles or quintiles, etc. For example, a median biomarker level can be used to define a cut-off value between a upper middle quartile values and lower middle quartile values, with the upper quartile and upper middle quartile representing roughly equal numbers of biomarker values from the subject population that are above the median, and the lower middle quartile and lower quartile representing roughly equal numbers of biomarker values below the median value. Evaluation of PAD risk can be assessed by, for example, assigning a subject to a quartile/quintile according to assessed biomarkers levels, where the quartile/quintile associated with the highest B2M, CRP, Cystatin C and glucose (and/or hemoglobin A1c) levels represents the highest risk of PAD.

After all the measurements are taken into account, the points may be added up or transformed by an algorithm into a value that correlates with, e.g., low risk of disease, moderate risk of disease, or high risk of disease. In the case of complex classification algorithms, it may be necessary to perform the algorithm on the data, thereby determining the classification, using a computer, e.g., a programmable digital computer. In either case, one can then record the status onto a tangible medium, e.g., a computer-readable format such as a memory drive or disk or simply printed on paper. The result also could be reported on a computer screen.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1—specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

A test that has a high sensitivity but a low specificity may still be useful if its negative predictive value is high enough to exclude a diagnosis of PAD. An example of a clinically very useful test that has high sensitivity but low specificity is the ventilation-perfusion scan. A negative test virtually excludes pulmonary embolism since the negative predictive value is over 95%. Such a test result can reduce the need for further and more expensive testing.

β2-microglobulin, hsCRP, cystatin C and glucose are differentially present in subjects with peripheral artery disease. While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile," "biomarker fingerprint," or "biomarker panel." Accordingly, a biomarker panel comprising β2-microglobulin, hsCRP, cystatin C and glucose (or hemoglobin A1c) can be combined with other biomarkers for peripheral artery disease to improve the sensitivity and/or specificity of the diagnostic test. Examples of other biomarkers useful for screening for PAD are found in the PCT Application US2005/018728 (Inter. Pub. No. WO2005/121758), filed May 26, 2005.

Presence of Disease

In one embodiment, this invention provides methods for assessing the risk of peripheral artery disease in a subject (status: peripheral artery disease v. non-peripheral artery disease). The risk of peripheral artery disease is determined by measuring the relevant biomarker or biomarkers and then either submitting them to a classification algorithm or comparing them with a reference amount and/or pattern of biomarkers that is associated with the particular risk level.

Determining Risk of Developing Disease

In one embodiment, this invention provides methods for determining the risk of developing peripheral artery disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level Determining Severity of Disease In one embodiment, this invention provides methods for determining the severity of peripheral artery disease in a subject. A subject with peripheral artery disease will have a characteristic pattern of biomarker levels depending on the severity of the disease. Disease severity may be determined by measuring the relevant biomarkers and then submitting the measured amounts to a classification algorithm, or measuring the relevant biomarkers and then comparing them with a reference amount and/or pattern of biomarkers associated with a degree of severity of the disease. For example, one can classify between mild, moderate, and severe peripheral artery disease, as well as non-peripheral artery disease. An index of severity based on the biomarker panel of the invention can likewise be used to predict the likelihood of future cardiovascular events such as stroke, myocardial infarction, and loss of limb.

Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, high beta-2-microglobulin levels, high cystatin C levels, high hsCRP levels, and high glucose (and/or hemoglobin A1c) levels are correlated with PAD. Therefore, the trend of these markers, either increased or decreased over time toward diseased or non-diseased, can be used to monitor the course of the disease. Accordingly, this method involves measuring one or more biomarkers in a subject for at least two different time points, e.g., a first time and a second time, and comparing the change in amounts, if any. The course of disease is determined based on these comparisons.

Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on measurements of $\beta$2-microglobulin, cystatin C, hsCRP and glucose (or, in some instances, hemoglobin A1c/glycated hemoglobin) in a test subject is communicated to the subject after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Subject Management

In certain embodiments of the methods of qualifying or assessing peripheral artery disease status, the methods further comprise managing subject treatment based on the status. Such management includes the actions of the physician or clinician subsequent to determining peripheral artery disease status. For example, if a physician makes a diagnosis of peripheral artery disease, then a certain regimen of treatment may follow. A suitable regimen of treatment may include, without limitation, a supervised exercise program; control of blood pressure, sugar intake, and/or lipid levels; cessation of smoking, including any necessary counseling and nicotine replacement; and drug therapies including the administration of aspirin (with or without dipyridamole), clopidogrel, cilostazol, and/or pentoxifylline; and/or an angiotensin converting enzyme inhibitor; and/or a beta-adrenergic antagonist (medications which have been shown to prolong the lives of individuals with PAD include anti-platelet agents, statins, ACE inhibitors and beta-adrenergic antagonists). Alternatively, a diagnosis of PAD might be followed by further testing to determine whether a patient is suffering from a specific form of PAD, or whether the patient is suffering from related diseases such as coronary artery disease. Also, if the diagnostic test gives an inconclusive result on PAD status, further tests may be called for.

Generation of Classification Algorithms for Qualifying Peripheral Artery Disease Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from timeof-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Pat. No. 6,675,104 (Paulse et al., "Method for analyzing mass spectra").

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method for analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for peripheral artery disease. The classification algorithms, in turn, form the base for diagnostic tests by providing diagnostic values (e.g., cut-off points) for biomarkers used singly or in combination.

Composition of Matter

In another aspect, this invention provides compositions of matter based on the biomarker panel of this invention, e.g., β2-microglobulin, cystatin C, hsCRP, glucose (and/or hemoglobin A1c or an equivalent proxy for glucose levels).

In one embodiment, this invention provides the biomarker of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. The biomarkers can be isolated from biological fluids, such as urine or serum. Biomarkers may be purified using any method known in the art, including, but not limited to, mechanical separation (e.g., centrifugation), ammonium sulphate precipitation, dialysis (including size-exclusion dialysis), electrophoresis (e.g. acrylamide gel electrophoresis) size-exclusion chromatography, affinity chromatography, anion-exchange chromatography, cation-exchange chromatography, and metal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

Kits for Detection of Biomarkers for Peripheral Artery Disease

In another aspect, the present invention provides kits for qualifying peripheral artery disease status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as Proteinchip® arrays. In the case of biospecfic capture reagents, the kit can comprise a solid support with a reactive surface, and a container comprising the biospecific capture reagent (e.g., an antibody that recognizes beta2-microglobulin, hsCRP or cystatin C).

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support. The kit can also comprise antibodies against one or more of the biomarkers, or reagents for detecting the activity or presence of the biomarker.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on PAD, the amounts or relative amounts (e.g., the pattern or profile) of β2-microglobulin and/or cystatin C and/or hsCRP and/or glucose should be observed to change toward a non-disease profile. For example, in patients with PAD, β2-microglobulin is increased. Therefore, one can follow the effect of treatment of the PAD patient by monitoring the corresponding levels of β2-microglobulin and/or the other biomarkers disclosed herein. Accordingly, this method involves measuring one or more biomarkers in a subject receiving drug therapy, and correlating the amounts of the biomarkers with the disease status of the subject. One embodiment of this method involves determining the levels of the biomarkers for at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

Use of Biomarkers for Peripheral Artery Disease in Screening Assays and Methods of Treating Peripheral Artery Disease The methods of the present invention have other applications as well. For example, the biomarkers can be used to screen for compounds that modulate the expression of the biomarkers in vitro or in vivo, which compounds in turn may be useful in treating or preventing peripheral artery disease in patients. In another example, the biomarkers can be used to monitor the response to treatments for peripheral artery disease. In yet another example, the biomarker panel can be used in heredity studies to determine if the subject is at risk for developing peripheral artery disease.

The invention is further illustrated by the Examples which follow.

EXAMPLES

Example 1

Discovery of Biomarkers for PAD

Some of the PAD biomarkers of the present invention were initially identified as such in a screening study using SELDI technology employing Proteinchip arrays from Ciphergen Biosystems, Inc. (Fremont, Calif.) ("Ciphergen"). The study set consisted of 45 patients with PAD and 43 patients without PAD. Subjects placed in the PAD group were those with an ankle-brachial index of 0.9 or less. Patients in the PAD group were slightly older and generally had higher frequencies of cardiovascular risk factors.

Plasma samples were obtained from subjects in a fasting state. Each plasma sample was subjected to fractionation on a QhyperDF column before analysis using Ciphergen's Proteinchips, as described in the detailed protocol below. After fractionation, selected fractions were analyzed using Ciphergen's IMAC30 or CM10 Proteinchips. The spectra of polypeptides in the samples were generated by time-of-flight mass spectrometry on a Ciphergen PBSII mass spectrometer. Peak intensity values (1619 peaks/sample) were analyzed by Statistical Analysis of Microarrays (SAM) software.

The present study differs from studies which purport to show a relationship between $\beta_2$-microglobulin levels and symptoms such as arterial stiffness (see, e.g., Saijo et al., *Hypertens. Res.*, 28(6):505-511 (2005)). Those studies excluded from their trials subjects diagnosed with PDA and patients with low ABI (<0.9). Also, the studies relied on a pulse wave velocity (PWV) assay for including/excluding patients. The PWV assay measures vascular compliance and not arterial disease per se. While the arteries in the subjects used in Saijo et al.'s trials may have been less compliant than those of a "normal" subject, they were not necessarily the narrowed and/or clogged arteries of subjects with PAD.

Representative fractionation, sample handling, and data acquisition protocols used to identify biomarkers, are described elsewhere, e.g., International Patent Publication WO 2005/121758 A1. Significance Analysis for Microarrays software ("SAM") was used to identify a set of significant peaks obtained from mass spectrometry of plasma samples as described above. SAM is described in detail in Tusher et al. (*PNAS* (2001) 98: 5116-5121). Table 2 summarizes 11 out of 1619 biomarkers that were identified as differing significantly between the PAD and non-PAD groups.

TABLE 2

Exact P values of linear regresson between the peak intensities and the ABI for selected differentially expressed proteins in discovery data sets

| m/Z | Conditions | Putative protein | Mean Peak Intensities | | | Correlation with ABI | |
|---|---|---|---|---|---|---|---|
| | | | PAD | Control | P value | rs | P |
| 11,732 | CM10-pH7 | Beta-2-microglobulin | 2.842 ± 0.167 | 2.028 ± 0.116 | <0.001 | −0.491 | <0.001 |
| 11,731 | CM10-pH7 | Beta-2-microglobulin | 9.902 ± 0.489 | 7.769 ± 0.454 | 0.002 | −0.419 | <0.001 |
| 11,722 | IMAC30-pH7 | Beta-2-microglobulin, most likely | 11.367 ± 0.716 | 8.644 ± 0.588 | 0.004 | −0.366 | 0.001 |
| 11,731 | IMAC30-pH5 | Beta-2-microglobulin | 13.883 ± 1.613 | 7.543 ± 0.484 | <0.001 | −0.401 | <0.001 |
| 11,811 | IMAC30-pH9 | Beta-2-microglobulin, most likely | 24.915 ± 0.883 | 21.214 ± 0.928 | 0.005 | −0.287 | 0.007 |
| 11,941 | IMAC30-pH5 | Beta-2-microglobulin, SPA adduct | 3.943 ± 0.353 | 2.543 ± 0.136 | <0.001 | −0.410 | <0.001 |
| 13,339 | CM10-pH9 | Cystatin C | 4.802 ± 0.291 | 3.662 ± 0.144 | 0.001 | −0.330 | 0.002 |
| 14,690 | CM10-pH9 | Lysozyme C | 2.975 ± 0.201 | 2.152 ± 0.147 | 0.02 | −0.374 | <0.001 |
| 22,519 | CM10-pH7 | most likely IgG light chain | 2.809 ± 0.119 | 2.211 ± 0.138 | <0.001 | −0.504 | <0.001 |
| 22,999 | CM10-organic | Not determined | 6.576 ± 0.311 | 5.3852 ± 0.247 | 0.004 | −0.351 | 0.001 |
| 36,067 | CM10-pH4 | Not determined | 0.477 ± 0.036 | 0.353 ± 0.016 | 0.003 | −0.225 | 0.037 |

Table 2 also includes the exact p values of linear regression analysis between ABI values and peak intensities for the selected differentially expressed proteins.

Western blots using anti-beta2 microglobulin antibody showed that higher beta 2-microglobulin concentrations were observed in samples from 4 patients with PAD compared to samples from 4 control subjects. This finding is consistent when using plasma fractionated at pH 5 or using whole, unfractionated plasma.

Confirmation Study

A confirmation study was conducted to confirm that the observed correlation was not confounded by other patient traits (e.g., other cardiovascular risk factors, renal function, etc.). For this confirmation study, plasma was obtained from 20 patients with PAD and 20 control subjects who had no clinical evidence of PAD or coronary disease. The patients in the two comparison groups were similar in age and gender. However, as expected, the PAD group had higher frequencies of cardiovascular risk factors and a trend toward lower glomerular filtration rate.

All plasma was obtained from patients in the fasting state. Beta 2-microglobulin was measured using a commercially available ELISA kit. The measurements showed that plasma and serum beta 2-microglobulin levels were significantly higher in PAD patients than control subjects, using a Mann-Whitney nonparametric test.

The results of a Spearman's Rank Correlation analysis showed a strong negative correlation (r<−0.5) between β2-microglobulin levels and ABI. A relationship was also observed between peak intensity of β2m and claudication time.

A linear regression analysis of the data showed that, among traditional risk factors for cardiovascular disease, a history of smoking, hyperlipidemia, and diabetes were statistically significant univariate predictors of ankle-brachial index. In addition, glomerular filtration rate had a positive trend toward a correlation with ankle-brachial index. β2-microglobulin, transformed logarithmically to reduce skewness, was strongly correlated with ankle-brachial index.

Using the listed variables, a multivariate model was created to assess the independent relationship between log β2-microglobulin and ankle-brachial index. This analysis confirmed an independent relationship between high βmicroglobulin levels and a lower ankle-brachial index. Specifically, the results showed that log β2-microglobulin levels remain independently associated in an inverse manner with the ankle-brachial index, even after adjustment for the potential confounding effects of lower glomerular filtration rates in PAD patients. This model predicted an estimated 45% of the variance of ankle-brachial index observed this study.

Validation Study in a Population at Risk for PAD

In patients undergoing coronary angiography, without known PAD status (n=237), serum β2m was higher in patients with PAD. ABI was determined prior to a comprehensive clinical characterization which included questionnaires to elicit demographics, ethnicity, quality of life, functional capacity; venipuncture for plasma, serum and genomic DNA; and coronary angiography. Patients with PAD had an ABI at rest of <0.90, or in those with non-compressible ankle arteries, a toe-brachial index of <0.60. Glomerular filtration rate (GFR) was estimated by the Modification of Diet in Renal Disease Study (MDRD) method 14. β2-microglobulin levels correlated with ABI independent of other vascular risk factors and GFR by multivariate regression analysis.

Example 2

A Biomarker Panel for PAD

Subjects. A total of 549 subjects for investigation were randomly selected from an ongoing peripheral artery disease study. The PAD status of these individuals was not known to the investigators at the time of informed consent and recruitment into the study. Ankle-brachial index (ABI) was determined immediately after recruitment, followed by a comprehensive clinical characterization which included coronary angiography. Patients with PAD had a resting ABI of <0.90 or, in those with non-compressible ankle arteries, a toe-brachial index of <0.60. Glomerular filtration rate (GFR) was estimated by the Modification of Diet in Renal Disease (MDRD) method (Levey et al., *Ann Intern Med* 1999; 130:461-70).

Coronary angiograms were reviewed by an experienced angiographer blinded to the subject's ABI. A significant coronary lesion was defined as an angiographic stenosis of ≧60% in any vessel.

Measurement of markers. Venipuncture was performed on fasting subjects and serum and plasma samples were stored at −75°. Glucose, high density lipoprotein cholesterol (HDL), triglycerides and total cholesterol were all measured by standard assays using an AU5400 Chemistry Immuno-Analyzer (Olympus Inc). Low density lipoprotein cholesterol (LDL) was measured by standard assay using AU640 Chemistry Immuno-Analyzer (Olympus). B2M (β2M), high sensitivity C-reactive protein (CRP) and Cystatin C assays were measured using standard nephelometry using BNII-Nephelometry system (Dade Behring Inc). All assay reagents were supplied by the relevant manufacturer with the exception of B2M nephelometric kit (The Binding Site Inc). Controls were purchased from Bio-Rad Laboratories or Cliniqa Corporation.

Data analysis and statistics. Dichotomous variables are expressed as prevalence in number and percent, and continuous data are expressed as the median (25th-75th percentiles). Univariate comparisons of risk factors and laboratory results were calculated using the Fisher exact test for dichotomous variables and using the nonparametric Mann-Whitney U test for continuous variables. Spearman coefficient of rank correlation was performed to assess the relationship of data to ABI. Calculations were performed using Prism 4.0 (Graphpad). Multiple linear regression was performed using all combinations of the markers to generate a multi-marker panel score that could predict ABI. Because the output of the linear regression analysis was positively correlated with ABI, the biomarker panel score was defined as the inverse of the linear regression output so that a higher score would indicate a higher risk. Logistic regression was used to investigate the relationship between the disease status and the biomarker panel score as well as other risk factors (e.g. age, diabetes status, smoking status). ROC analysis was performed to test the predictive power of the biomarker panel score. All subjects were assigned a score using the AHA Framingham risk score charts based on data obtained at recruitment.

The odds ratio was calculated in the logistic regression analysis. R was used in the linear regression analysis. SAS was used for logistic regression analysis and odds ratio calculation. Analyze-it was used for ROC analysis.

Results

All study participants underwent coronary angiography (n=549), and included a group with no hemodynamically significant atherosclerosis (NHSD; n=262); one with CAD+PAD (n=197); and a group with CAD alone (n=81). The NHSD group was younger than the CAD+PAD group. Also, as expected, the group with CAD+PAD had a significantly higher incidence of cardiovascular risk factors such as smoking, diabetes, and hypertension. The data summarized in Table 3 shows that biochemical markers for cardiovascular risk were higher in the CAD+PAD group than in the NHSD group.

Correlation analysis was performed to determine which characteristics were most highly associated with ABI. Table 4 shows that the traditional risk factors most strongly associated with PAD were diabetes status and age. Among biochemical markers, β2M and cystatin C correlated most strongly with ABI.

Linear regression using these variables was performed to generate indices for various combinations of two, three, and all four biomarkers. For the four marker index, each of the biomarkers is significant (p<0.001) in the model. These linear regression indices were positively correlated with ABI, i.e., a lower value of the linear regression index indicated lower ABI. The biomarker panel score was defined as the inverse of the linear regression index so that a higher biomarker panel score would indicate higher likelihood of positive PAD status. The odds ratio was calculated for each of the quartiles for each of the individual markers as well as for each of the combinations. This data is presented in Table 5. The panel score comprising all four markers had the highest odds ratio when comparing the highest quartile vs the lowest quartile, and its significance was still apparent even after adjusting for traditional risk factors of age, diabetes, and smoking. Table 5 shows that after adjusting for the traditional risk factors, individuals in the top quartile of the four marker index had a 7-fold greater chance of having PAD.

ROC analysis was performed to determine the diagnostic accuracy of the individual markers and marker combinations. The marker panel that encompassed all four markers (i.e., β2M, cystatin C, hsCRP, and glucose) performed the best in distinguishing the NHSD from the group subjects with both CAD and PAD. The AUC for the four marker panel was 0.747 (95% confidence interval 0.702-0.791). As shown in FIG. 1, a cutoff corresponding to the 75th percentile, the index had a sensitivity of 90.4% and specificity of 36.6%.

Because these results compare patients with CAD and PAD with those with no significant hemodynamic disease, the elevation in biomarkers might be associated with the pathophysiology of CAD, of PAD, or both. Thus, the series of individuals with only CAD (n=81) was compared to the CAD+PAD group. These groups were very similar with respect to the burden of the traditional risk factors, although diabetes and tobacco use were more prevalent in the CAD+PAD group. The mean value of each of the biomarkers, cystatin C, hsCRP and β2M were greater in the CAD+PAD group (Table 3). The biomarker panel score was able to distinguish between the CAD group and the CAD+PAD group, although the AUC of the ROC was lower than that obtained when comparing CAD+PAD vs NHSD groups (Table 6).

Figure 2:
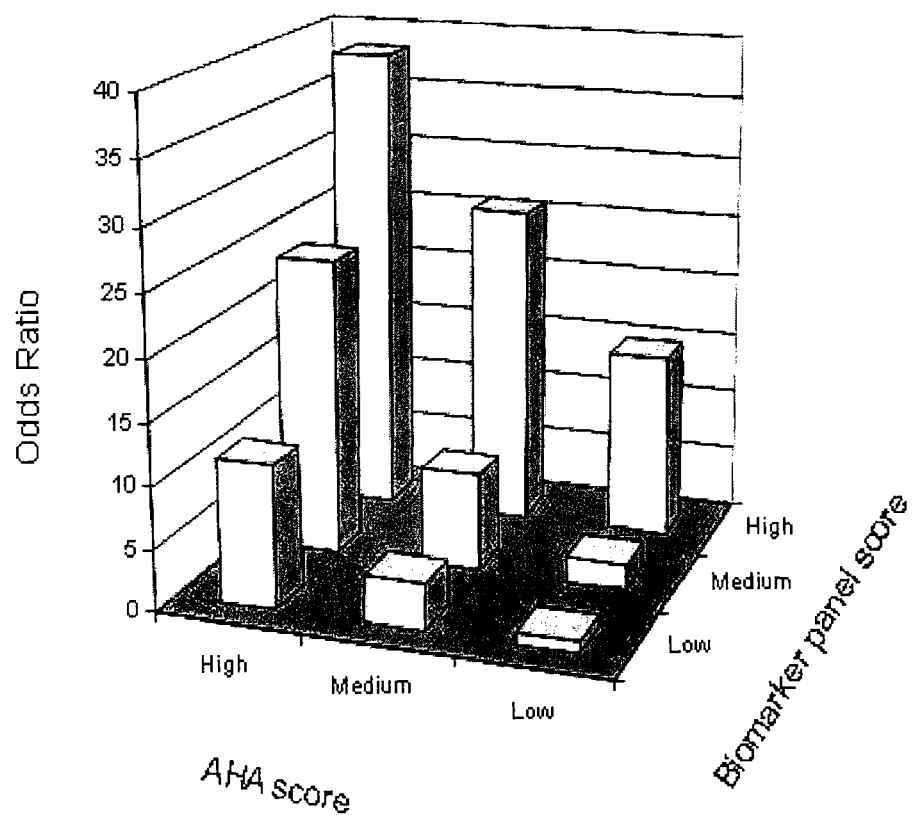
FIG. 2 presents the odds ratio of CAD+PAD status by AHA (American Heart Association) risk score and by biomarker panel score. There is a positive interaction between the two assessments of disease risk. Individuals were assigned an AHA risk score using the traditional cardiovascular risk factors as described by Wilson et al., *Circulation* 1998; 97:1837-47. AHA risk scores of <5 (low), 5 to 10 (medium) and >10 (high) were associated with increasing risk of PAD (p=0.006 for men and p<0.001 for women using the score from the linear regression by ANOVA). The tertile cutoffs of the biomarker panel score were used to determine the risk level: low (<0.991), medium (0.991-1.033), and high (>1.033).

The chart in FIG. 2 illustrates the odds ratio of CAD+PAD status in analyses in which study participants were stratified into nine groups according to the value of the AHA risk score and that of the four biomarker panel score. Individuals were assigned an AHA risk score using the traditional cardiovascular risk factors as described (Wilson et al., *Circulation* 1998; 97:1837-47). AHA risk scores of <5 (low), 5 to 10 (medium), and >10 (high) were associated with increasing risk of PAD (p=0.006 for men and <0.001 for women using the score from the linear regression by ANOVA). The odds ratio was calculated by comparing each of the 8 groups to the one with the lowest risk of disease (low AHA risk score and low biomarker panel score). As shown, there was a positive interaction between the two scores. Individuals with a low AHA risk score and a low biomarker panel score had the least risk of PAD. Individuals with a high AHA risk score and a high biomarker panel score had the greatest risk of PAD. Notably, individuals with a low AHA risk score had a considerable risk of PAD if they had a high biomarker panel score.

In summary, after adjustment for smoking, diabetes and age, the combination marker score was able to identify a group with an odds ratio greater than seven for PAD, in a population of patients referred for coronary angiography. Currently, clinical assessments of risk factor burden, such as the AHA risk score, incorporate "traditional" CV risk factors and are used to predict risk of future events. To the extent that the AHA risk score reflects the burden of CV risk factors, it approximates the clinician's assessment of the risk of vascular disease. Accordingly, the predictive power of the biomarker panel was compared to the accepted AHA risk score. We found a positive interaction between the biomarker panel and the AHA risk score. Subjects at highest risk were those with both a high AHA score, and a high biomarker panel score. Also, certain subjects having low AHA risk scores but high scores using the four biomarker panel disclosed herein were identifiable as subjects with a high risk of PAD. Thus, one use for the biomarkers and, in particular, the four biomarker panel disclosed herein is to identify a group of patients who are high risk for PAD that would otherwise be missed. Another use for the β2-microbulin, hsCRP, Cystatin C and/or glucose/hemoglobin A1c biomarkers described herein and, in particular, the four biomarker panel, is to further stratify the risk of PAD in patients known to be at risk of CAD. Such a stratification can be used to further inform a physician's diagnosis and/or enable the physician to treat a subject with the most effective and/or least harmful therapeutics.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 3

Subject Demographics and Biomarkers

| | NHSD (n = 262) | CAD/PAD (n = 197) | CAD (n = 81) | NHSD vs CAD/PAD | CAD/PAD vs CAD |
|---|---|---|---|---|---|
| Male sex (n, %) | 138 (53%) | 77 (39%) | 43 (46%) | 0.005 | 0.23 |
| Age, (years) | 63 (56-71) | 70 (64-77) | 72 (67-78) | <0.001 | 0.14 |
| Body mass index, (kg/m2) | 28.3 (24.7-33.1) | 27.9 (25.1-31.6) | 28.5 (25.9-31.8) | 0.3 | 0.32 |
| Smoking (n, %) | 119 (45%) | 135 (69%) | 45 (56%) | <0.001 | 0.05 |
| Hypertension (n, %) | 185 (71%) | 170 (86%) | 70 (86%) | <0.001 | 1.0 |
| Diabetes (n, %) | 52 (20%) | 89 (45%) | 22 (27%) | <0.001 | 0.007 |
| Resting ABI | 1.11 (1.02-1.19) | 0.79 (0.7-0.9) | 1.1 (1.0-1.14) | <0.001 | <0.001 |
| GFR | 86.3 (63.1-108) | 64.3 (46.7-84.6) | 71.4 (50.2-94.6) | <0.001 | 0.16 |
| B2M (mg/dl) | 1.67 (1.41-2.05) | 2.19 (1.7-3.4) | 1.9 (1.57-2.43) | <0.001 | 0.002 |
| Cystatin C (mg/dl) | 0.66 (0.58-0.77) | 0.83 (0.7-1.2) | 0.77 (.65-.89) | <0.001 | 0.016 |
| HsCRP (mg/l) | 1.5 (0.6-3.7) | 2.2 (0.9-6.3) | 1.4 (0.7-3.9) | <0.001 | 0.031 |
| Triglycerides (mg/dl) | 88 (63-131) | 105 (70.2-145) | 91.1 (68.9-130) | 0.007 | 0.166 |
| Total cholesterol (mg/dl) | 150 (125-173) | 138 (110-157) | 132 (107-152) | <0.001 | 0.184 |
| LDL cholesterol (mg/dl) | 85 (66-109) | 73 (58-95) | 77 (58-94) | <0.001 | 0.808 |
| HDL cholesterol (mg/dl) | 42 (34-51) | 38 (30-45) | 37 (30-46) | 0.003 | 0.91 |
| Glucose (mg/dl) | 85.4 (79.2-96.1) | 94.6 (82.7-130) | 91.1 (80.8-102) | <0.001 | 0.085 |

TABLE 4

Spearman Correlations Between Risk Factors, Biomarkers and ABI

| | r | 95% CI | p |
|---|---|---|---|
| Gender | −0.017 | −0.102, 0.069 | 0.69 |
| Age | −0.231 | −0.310, −0.148 | <0.001 |
| Body mass index, kg/m2 | 0.017 | −0.069, 0.102 | 0.694 |
| Smoking | −0.159 | −0.242, −0.075 | <0.001 |
| Hypertension | −0.148 | −0.230, −0.063 | <0.001 |
| Diabetes | −0.239 | −0.318, −0.157 | <0.001 |
| GFR | 0.238 | 0.155, 0.318 | <0.001 |
| B2M, mg/L | −0.297 | −0.373, −0.217 | <0.001 |
| Cystatin C, mg/L | −0.302 | −0.378, −0.222 | <0.001 |
| hsCRP, mg/L | −0.180 | −0.261, −0.096 | <0.001 |
| Triglycerides, mg/dL | −0.110 | −0.194, −0.025 | 0.009 |
| Total Chol, mg/dL | 0.031 | −0.055, 0.116 | 0.472 |
| LDL, mg/dL | 0.092 | 0.006, 0.176 | 0.031 |
| HDL, mg/dL | 0.001 | −0.084, 0.087 | 0.97 |
| Glucose, mg/dL | −0.200 | −0.281, −0.116 | <0.001 |

TABLE 5

Unadjusted and Adjusted Risks for the Diagnosis for PAD Based on Biomarkers.
(Data expressed as odds ratio, (95% confidence interval)

| Marker | Model 1 | Model 2 | Model 3 | Model 4 | Model 5 |
|---|---|---|---|---|---|
| β2M | 6.1* (3.0-12.2) | 3.2† (1.5-6.9) | 5.7* (2.8-11.6) | 5.4* (2.6-11.0) | 2.5§ (1.1-5.5) |
| Cystatin C | 5.6* (2.9-10.8) | 3.1* (1.5-6.2) | 5.3* (2.7-10.3) | 5.3* (2.7-10.3) | 2.6* (1.3-5.4) |
| hsCRP | 2.2† (1.2-3.8) | 2.8* (1.5-5.3) | 2.3† (1.3-4.0) | 1.9* (1.0-3.3) | 2.6† (1.3-4.9) |
| Glucose | 3.4* (1.9-6.0) | 1.5* (0.8-2.7) | 2.3§ (1.2-4.2) | 3.3* (1.8-5.8) | 1.8§ (0.9-3.5) |
| β2M + hsCRP | 3.2† (1.9-5.6) | 4.1* (2.3-7.5) | 3.1† (1.8-5.4) | 2.9§ (1.6-5.0) | 3.6§ (1.9-6.8) |
| β2M + Cystatin C | 5.9* (3.3-10.4) | 4.1† (2.3-7.5) | 5.6* (3.1-10.0) | 5.6* (3.1-10.0) | 3.5§ (1.9-6.7) |
| β2M + Glucose | 5.7* (3.2-10.1) | 5.7* (3.1-10.5) | 3.9* (2.1-7.2) | 5.5* (3.1-10.0) | 3.6§ (1.8-7.1) |
| hsCRP + Cystatin C | 6.9* (3.8-12.4) | 6.7* (3.6-12.6) | 6.6* (3.6-12.2) | 6.2* (3.3-11.4) | 6.1* (3.1-12.0) |
| hsCRP + Glucose | 5.9* (3.3-10.4) | 6.3* (3.4-11.5) | 4.3† (2.4-7.9) | 5.5† (3.0-9.9) | 4.1§ (2.1-7.9) |
| Cystatin C + Glucose | 6.8* (3.8-12.1) | 6.3* (3.4-11.6) | 4.9* (2.6-9.1) | 6.4* (3.5-11.6) | 3.9§ (2.0-7.8) |
| β2M + hsCRP + Cystatin C | 6.8* (3.8-12.1) | 5.2* (2.8-9.5) | 6.7* (3.7-12.2) | 6.1* (3.4-11.1) | 4.6* (2.4-8.8) |
| β2M + hsCRP + Glucose | 5.6* (3.2-9.9) | 6.4* (3.5-11.8) | 4.1† (2.3-7.5) | 5.2† (2.9-9.3) | 4.2§ (2.2-8.3) |

TABLE 5-continued

Unadjusted and Adjusted Risks for the Diagnosis for PAD Based on Biomarkers.
(Data expressed as odds ratio, (95% confidence interval)

| Marker | Model 1 | Model 2 | Model 3 | Model 4 | Model 5 |
|---|---|---|---|---|---|
| hsCRP + Cystatin C + Glucose | 6.8* (3.8-12.1) | 6.9* (3.7-12.8) | 5.0* (2.7-9.3) | 6.2* (3.4-11.3) | 4.5§ (2.3-8.8) |
| β2M + Cystatin C + Glucose | 10.8* (5.9-20.1) | 8.4* (4.4-15.9) | 8.4* (4.4-16.0) | 10.0* (5.4-18.9) | 5.4* (2.7-10.8) |
| β2M + hsCRP + Cystatin C + Glucose | 12.4* (6.6-23.5) | 11.7* (6.0-22.6) | 9.4* (4.8-18.2) | 11.2* (5.9-21.4) | 7.3* (3.6-14.9) |

Model 1: Unadjusted
Model 2: Adjusted for age
Model 3: Adjusted for diabetes status
Model 4: Adjusted for smoking
Model 5: Adjusted for age, diabetes, smoking
*p < 0.001
†p < 0.01
§p < 0.05

TABLE 6

Area Under the Curve Derived from Receiver-Operator Curves
for the Diagnosis of PAD Using Combination Biomarkers

| Marker | NHSD vs CAD + PAD | CAD vs CAD + PAD |
|---|---|---|
| β2M | 0.697 (0.648, 0.746) | 0.613 (0.544, 0.681) |
| Cystatin C | 0.704 (0.655, 0.752) | 0.593 (0.524, 0.662) |
| hsCRP | 0.593 (0.54, 0.645) | 0.583 (0.511, 0.655) |
| Glucose | 0.637 (0.585, 0.69) | 0.563 (0.492, 0.633) |
| β2M + HsCRP | 0.617 (0.565, 0.668) | 0.600 (0.529, 0.671) |
| β2M + Cystatin C | 0.690 (0.641, 0.74) | 0.557 (0.486, 0.627) |
| β2M + Glucose | 0.677 (0.627, 0.726) | 0.606 (0.536, 0.675) |
| hsCRP + Cystatin C | 0.669 (0.62, 0.718) | 0.612 (0.542, 0.682) |
| hsCRP + Glucose | 0.683 (0.632, 0.733) | 0.627 (0.559, 0.696) |
| Cystatin C + Glucose | 0.709 (0.66, 0.757) | 0.623 (0.554, 0.691) |
| β2M + hsCRP + Cystatin C | 0.693 (0.644, 0.741) | 0.589 (0.52, 0.659) |
| β2M + hsCRP + Glucose | 0.691 (0.642, 0.741) | 0.639 (0.571, 0.707) |
| β2M + Cystatin C + Glucose | 0.734 (0.687, 0.781) | 0.608 (0.539, 0.676) |
| hsCRP + Cystatin C + Glucose | 0.719 (0.671, 0.766) | 0.65 (0.583, 0.717) |
| β2M + hsCRP + Cystatin C + Glucose | 0.747 (0.702, 0.791) | 0.636 (0.568, 0.703) |

What is claimed is:

1. A method for diagnosing peripheral artery disease in a subject, comprising: measuring levels of beta-2-microglobulin, cystatin C, hsCRP, and at least one additional biomarker selected from the group consisting of glucose, hemoglobin A1c and glycated hemoglobin in a biological sample of the subject; comparing said measurements to a standard, wherein an increase in said levels of beta-2-microglobulin, cystatin C, hsCRP, and said at least one additional biomarker relative to said standard is associated with an increased risk of peripheral artery disease in a subject; and reporting or recording the results of said comparison.

2. A method for diagnosing peripheral artery disease in a subject, comprising: measuring levels of beta-2-microglobulin, cystatin C, hsCRP, and at least one additional biomarker selected from the group consisting of glucose, hemoglobin A1c and glycated hemoglobin in a biological sample of the subject; combining the measured levels to derive an index score; comparing said index score with a standard, wherein said comparison identifies a risk of peripheral artery disease in a subject; and reporting or recording the results of said comparison.

3. The method of claim 1 or 2, further comprising determining the risk of coronary artery disease in said subject.

4. The method of claim 3, wherein said determining the risk of coronary artery disease in said subject comprises the use of a scoring sheet.

5. The method of claim 3, wherein the risk of coronary artery disease in said subject is determined to be low.

6. The method of claim 1 or 2, wherein said levels of beta-2-microglobulin, cystatin C, hsCRP, hemoglobin A1c or glycated hemoglobin are measured by antibody or activity assays.

7. The method of claim 2, wherein a computer algorithm is utilized to calculate said index score.

8. The method of claim 2, further comprising a step of categorizing said index score as falling into one of at least three categories of increasing risk.

9. The method of claim 2, wherein said index score as categorized as falling into one of a tertile corresponding to low, medium and high risk of PAD.

10. The method of claim 2, further comprising utilizing said index score to assess the impact on a subject of a treatment for PAD.

11. A method for diagnosing peripheral artery disease in a patient previously diagnosed with coronary artery disease or a risk thereof, comprising: measuring levels of .beta.-2-microglobulin, cystatin C, and hsCRP; and at least one additional biomarker selected from the group consisting of glucose, hemoglobin A1c and glycated hemoglobin in a biological sample of the subject, and comparing said measurements to a standard, wherein an increase in said levels relative to said standard is associated with an increased risk of peripheral artery disease in a subject; and reporting or recording the results of said comparison.

* * * * *